(12) United States Patent
Singh et al.

(10) Patent No.: US 8,335,571 B2
(45) Date of Patent: Dec. 18, 2012

(54) INDUCTIVE ELEMENT FOR INTRAVASCULAR IMPLANTABLE DEVICES

(75) Inventors: Udai Singh, Cary, NC (US); Stephen C. Masson, Raleigh, NC (US)

(73) Assignee: Synecor, LLC., Durham, NC (US)

( * ) Notice: Subject to any disclaimer, the term of this patent is extended or adjusted under 35 U.S.C. 154(b) by 0 days.

(21) Appl. No.: 13/295,916

(22) Filed: Nov. 14, 2011

(65) Prior Publication Data
US 2012/0130441 A1 May 24, 2012

Related U.S. Application Data

(62) Division of application No. 11/833,101, filed on Aug. 2, 2007, now Pat. No. 8,060,218.

(51) Int. Cl.
*A61N 1/05* (2006.01)
(52) U.S. Cl. ........................................................ 607/116
(58) Field of Classification Search .................. 607/115, 607/116
See application file for complete search history.

(56) References Cited

U.S. PATENT DOCUMENTS

| | | |
|---|---|---|
| 4,841,201 A | 6/1989 | Takizawa et al. |
| 5,220,929 A | 6/1993 | Marquit |
| 5,251,624 A | 10/1993 | Bocek et al. |
| 5,265,588 A | 11/1993 | Nelson et al. |
| 5,405,367 A | 4/1995 | Schulman et al. |
| 5,447,522 A | 9/1995 | Chang et al. |
| 5,583,421 A | 12/1996 | Barbehenn et al. |
| 5,682,306 A | 10/1997 | Jansen |
| 5,694,302 A | 12/1997 | Faulk |
| 5,757,167 A | 5/1998 | Arora et al. |
| 5,786,990 A | 7/1998 | Marrero |
| 5,901,433 A | 5/1999 | Moon et al. |
| 5,994,880 A | 11/1999 | Dropps |
| 6,094,597 A | 7/2000 | Wold |
| 6,442,413 B1 | 8/2002 | Silver |
| 6,477,414 B1 | 11/2002 | Silvian |
| 6,496,733 B2 | 12/2002 | Zarinetchi et al. |
| 6,600,667 B2 | 7/2003 | Francescutti et al. |
| 6,661,875 B2 | 12/2003 | Greenwald et al. |
| 6,876,287 B2 | 4/2005 | Matsuura et al. |
| 6,879,237 B1 | 4/2005 | Viarouge et al. |
| 6,914,513 B1 | 7/2005 | Wahlers et al. |
| 6,933,822 B2 | 8/2005 | Haugs et al. |

(Continued)

FOREIGN PATENT DOCUMENTS

WO    WO 01/47324    6/2001

(Continued)

OTHER PUBLICATIONS

Written Opinion of the International Searching Authority for International Application No. PCT/US2008/071962; dated Feb. 23, 2009.

(Continued)

*Primary Examiner* — Brian T Gedeon
(74) *Attorney, Agent, or Firm* — Patterson Thuente Christensen Pedersen, P.A.

(57) ABSTRACT

An inductive element adapted for use in implantable intravascular devices (IIDs) having an elongate form factor with a cross-section. The inductive element includes a core that has an outer surface contour that corresponds to the form factor. A set of elongate, or oblong, windings are situated lengthwise along the major length dimension of the inductive element. The windings are also situated to direct a magnetic field along a radial direction in relation to the elongate form factor. In one embodiment the form factor is generally cylindrical and the cross-section is generally round.

6 Claims, 14 Drawing Sheets

U.S. PATENT DOCUMENTS

| | | |
|---|---|---|
| 7,023,714 B2 | 4/2006 | Ceruti et al. |
| 7,030,596 B1 | 4/2006 | Salerno et al. |
| 7,072,171 B1 | 7/2006 | Muffoletto et al. |
| 7,082,336 B2 | 7/2006 | Ransbury et al. |
| 7,097,665 B2 | 8/2006 | Stack et al. |
| 7,231,260 B2 | 6/2007 | Wallace et al. |
| 7,242,982 B2 | 7/2007 | Singhal et al. |
| 7,616,997 B2 | 11/2009 | Kieval et al. |
| 2002/0161406 A1 | 10/2002 | Silvian |
| 2004/0015199 A1 | 1/2004 | Thompson et al. |
| 2004/0207503 A1 | 10/2004 | Flanders et al. |
| 2004/0215243 A1 | 10/2004 | Houben et al. |
| 2004/0215279 A1 | 10/2004 | Houben et al. |
| 2004/0249417 A1 | 12/2004 | Ransbury et al. |
| 2005/0018455 A1 | 1/2005 | Ceruti et al. |
| 2006/0114094 A1 | 6/2006 | Jean et al. |
| 2007/0288076 A1 | 12/2007 | Bulkes et al. |

FOREIGN PATENT DOCUMENTS

| | | |
|---|---|---|
| WO | WO 03/049269 | 6/2003 |
| WO | WO 2004/006037 | 1/2004 |
| WO | WO 2005/000398 | 4/2005 |
| WO | WO 2006/102290 | 9/2006 |

OTHER PUBLICATIONS

International Search Report for International Application No. PCT/US2008/071962; dated Feb. 23, 2009.

U.S. Appl. No. 11/833,101, filed Aug. 2, 2009; Udai Singh et al.

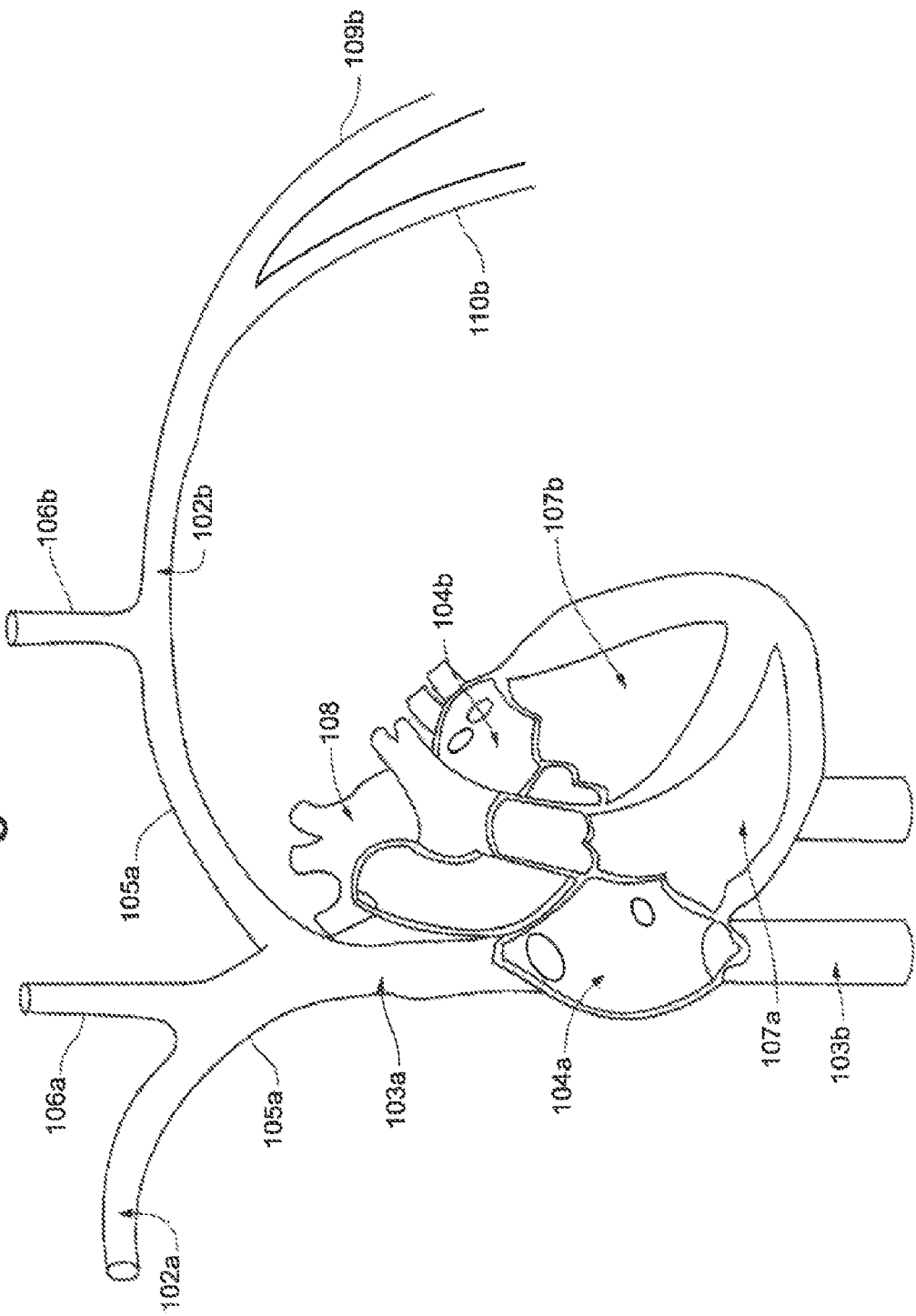

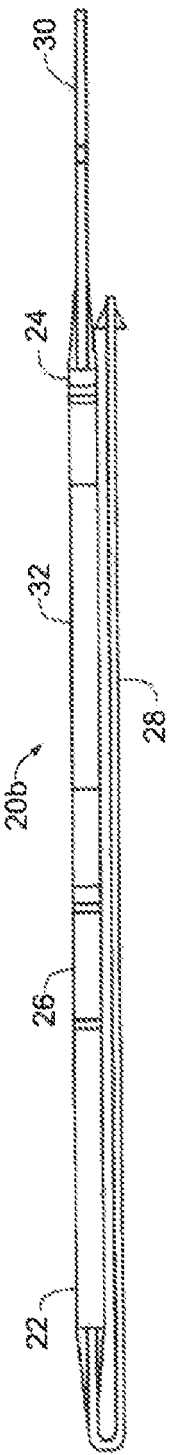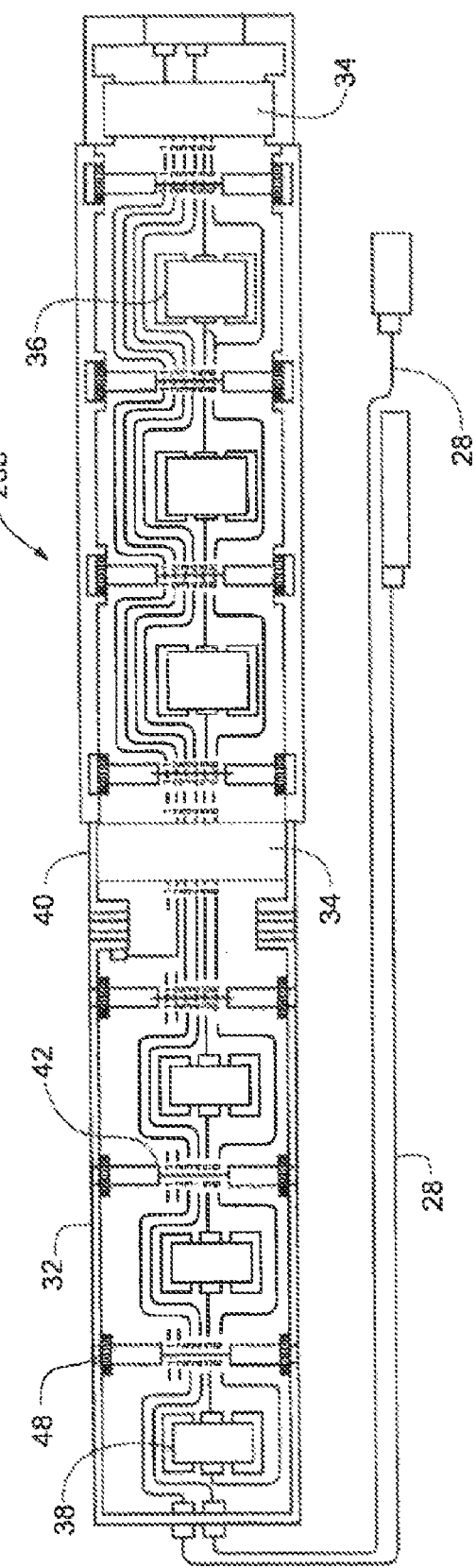
Fig. 3A
Fig. 3B

INDUCTIVE ELEMENT FOR INTRAVASCULAR IMPLANTABLE DEVICES

RELATED APPLICATIONS

This application is a divisional of U.S. application Ser. No. 11/833,101 now U.S. Pat. No. 8,060,218, filed Aug. 2, 2007, the disclosure of which is hereby incorporated by reference in its entirety.

FIELD OF THE INVENTION

The present invention relates generally to electrical components and, more particularly, to an inductive element, such as a choke or transformer, that has a narrow form factor suitable for use in implantable medical devices such as intravascular devices.

BACKGROUND OF THE INVENTION

Implantable medical devices such as pacemakers, defibrillators, and implantable cardioverter defibrillators ("ICDs") have been successfully implanted in patients for years for treatment of heart rhythm conditions. Pacemakers are implanted to detect periods of bradycardia and deliver low energy electrical stimuli to increase the heart rate. ICDs are implanted in patients to cardiovert or defibrillate the heart by delivering high energy electrical stimuli to slow or reset the heart rate in the event a ventricular tachycardia (VT) or ventricular fibrillation (VF) is detected. Another type of implantable device detects an atrial fibrillation (AF) episode and delivers electrical stimuli to the atria to restore electrical coordination between the upper and lower chambers of the heart. Still another type of implantable device stores and delivers drug and/or gene therapies to treat a variety of conditions, including cardiac arrhythmias. The current generation for all of these implantable devices are typically can-shaped devices implanted under the skin that deliver therapy via leads that implanted in the heart via the patient's vascular system.

Next generation implantable medical devices may take the form of elongated intravascular devices that are implanted within the patient's vascular system, instead of under the skin. Examples of these intravascular implantable devices are described, for example, in U.S. Pat. No. 7,082,336, U.S. Publ. Appl. Nos. 2005/0043765A1, 2005/0208471A1 and 2006/0217779A1. Devices of this type can have a diameter of about 3-15 mm and a length of about 10-60 cm to facilitate insertion and implantation inside of the vasculature, while permitting a sufficient amount of blood flow around the device. Within geometric constraints such as these, the devices contain electrical/electronic components and circuitry for performing their various functions.

Implantable devices have on-board energy storage (typically, batteries), and high voltage converter circuits for converting the stored energy into a form suitable for operating the device to deliver electrotherapy therapy. In cardioverter/defibrillator-type devices, the high voltage converter circuitry typically includes a circuit that produces energy at high voltage (typically at least in the range of 50-800 Volts and 1-40 Joules) for use in the application of the cardioversion/defibrillation electrotherapy. Because there is only a finite amount of energy available in the energy storage, and because replacing the batteries typically involves a surgical procedure to remove or otherwise access the implanted device or a recharge process that can require extended periods of time for recharging the energy storage, providing highly efficient circuitry is important to prolonging the useful life of the device and also to making the device as small as practicable. Accordingly, the high voltage converter circuit used in implantable devices should be as efficient as possible.

A switching mode power converter is generally considered to be one of the most efficient arrangements for stepping up voltage from the energy storage to the high voltage required for delivery of the electrotherapy. This type of converter operates by applying intermittent current to an inductive element such as a choke or a transformer, and harnessing the voltage-boosting effect produced by the associated time-varying magnetic field generated by the inductive element. A variety of switching converter topologies and operating modes are well-known. Examples include the boost converter, the flyback converter, the SEPIC (single-ended primary inductance converter), and the Cuk converter. The boost converter and certain Cuk converter topologies use one or more inductors, whereas the flyback, SEPIC, and other types of Cuk converters use transformers as the principal inductive elements for performing the voltage conversion function. Certain SEPIC topologies use both, an inductor, and a transformer.

The inductive element (whether an inductor or a magnetically coupled set of inductors) is generally constructed from at least one coil of wire and a magnetic core of high relative permeability material, such as ferromagnetic material. The core operates to confine the magnetic field closely to the element, thereby increasing its inductance. The core provides a magnetic flux path that guides the flux through the center of the coil(s) and along a return path that can be contiguous, or can alternatively have a plurality of non-contiguous return path portions. A variety of core geometries are known for inductive elements. Some are constructed as enamel coated wire wrapped around a ferrite bobbin with wire exposed on the outside, while others enclose the wire completely in ferrite for improved shielding effect. Core geometries typically include toroidal structures, C- or E-shaped structures, pot-shaped structures and planar structures.

In the case of a switching mode transformer, a typical turns ratio for use in a high voltage converter circuit for an implantable device can be on the order of Np:Ns being 1:15, where Np is the number of primary turns and Ns is the number of secondary turns. Unlike transformers used for signals and linear power supplies, transformers used in switching mode circuits are designed not only to transfer energy, but also to store the energy for a significant fraction of the switching period. For instance, in a power converter switching at about 60 kHz (which is a frequency selected to keep core eddy current losses low) and having a transformer with a core made from a power ferrite material with relative permeability of 2000 to 4000, a certain minimum primary inductance is required in the transformer.

Most of the stored energy in an inductive element is stored in an air gap of the core. A certain air gap volume is needed to store the desired energy. However, increasing the gap length reduces the inductance in the transformer or inductor. Winding inductance in an inductive element is directly proportional to the square of the number of windings, and to the magnetic cross sectional area orthogonal to the direction of magnetic flux produced in the volume. To compensate for the loss of inductance due to an increased air gap, a greater number of windings or a greater cross-sectional area for the magnetic flux path is needed. More windings take up more volume, and increase the power losses in the device due to increased resistance. Increasing the cross-sectional area for the magnetic flux path in a conventional core geometry would involve increasing the size of the core and consequently taking space away from the windings or increasing the overall size of the device.

In terms of an intravascular implantable device which may take the form of an elongated structure implanted within a patient's vasculature and generally having a circular cross-sectional area, if a standard circular pot core is used as the ferrite core of the transformer, the magnetic cross sectional area will be limited to something less than the cross-sectional area of the implantable device. Given this limitation, one alternative to increasing inductance is to increase the number of windings. Unfortunately, this adds to the winding volume in the transformer as a relatively high windings turns-ratio is needed for the high voltage converter. Aside from the higher overall resistance in the windings by increasing the total number of turns, this approach would also require a longer transformer to accommodate the windings.

A long and narrow pot core poses difficult winding challenges when used in an implantable intravascular device owing to the limited winding cross sectional area across the diameter of the core. Furthermore, there is a practical limit to the length of the transformer in implantable intravascular devices. For instance, the housing of the implantable intravascular device must provide a certain amount of flexibility to facilitate routing of the device through the vasculature. Longer sections of rigid housing elements limit the flexing radius of the device. In addition, the enclosure section housing the transformer may need space beyond the ends of the transformer to house circuitry, input/output hardware, wiring, and the like.

Other approaches, such as scaling down an E core or one of its derivatives, such as the EFD or ER cores, for use within the dimensional confines of an intravascular device may not be feasible given the energy storage and inductance requirements for the power converter circuit. For instance, there may be insufficient winding area to achieve the target primary inductance for a transformer. Even if the electrical performance were achievable in the small size, using a scaled-down E core-type inductive element in the intravascular device's housing would be wasteful of housing volume because excess volume would remain in the housing around the inductive element.

Given the size constraints of intravascular implantable devices, designing a power converter that can effectively and efficiently generate the high voltage electrotherapy signals using present-day inductive elements presents significant challenges. Typical core shapes and geometries, such as the E, C, toroidal, and pot cores ordinarily capable of providing the required functional and performance requirements for high voltage converters in conventional implantable device like conventional can-shaped implantable defibrillators are not well-suited for use in the small-diameter space of implantable intravascular devices.

SUMMARY OF THE INVENTION

The present invention is generally directed to an inductive element adapted for use in implantable intravascular devices (IIDs) having an elongate form factor adapted for implantation in the vasculature. The inductive element includes a core that has an outer surface contour that corresponds to an interior surface contour of a form factor of the IID. A set of elongate, or oblong, windings are situated lengthwise along the major length dimension of the inductive element. The windings are also situated to direct a magnetic field along a radial direction in relation to the longitudinal axis of the form factor of the IID.

In one aspect of the present invention, an implantable intravascular medical device includes a structure that defines a form factor having an elongate geometry including a length and a generally round cross-section, the cross-section being defined perpendicularly to the length. One example of such a structure is a housing, or a portion of an enclosure that provides a hermetic barrier, and has a generally cylindrical form factor suitable for implantation in the vasculature. A circuit is situated within the form factor and includes an energy storage device, such as a battery, and a converter circuit that operates to convert an output of the energy storage device into a relatively higher voltage. The converter circuit includes an inductive element that has an outer surface of a shape that corresponds to the form factor. The inductive element has a coil positioned to direct a magnetic field generally perpendicularly to the length.

An implantable intravascular medical device according to another aspect of the present invention includes a structure that defines a form factor having an elongate geometry including a form factor length and a generally round form factor cross-section defined perpendicularly to the form factor length. A circuit is situated within the form factor and has an inductive element, which includes a core of magnetic material having a core length and a core cross-section defined perpendicularly to the length, and a coil having a plurality of windings that define a loop area. A portion of the core is situated in the loop area such that the coil, when energized, produces a magnetic flux in the core along a forward path and a return path. A sum of a total cross-sectional area of the magnetic flux in the forward path and a total cross-sectional area of the magnetic flux in the return path is greater than an area of the core cross-section.

An inductive element (e.g., an inductor or transformer) according to one aspect of the invention includes a core of magnetic material having a core length and a generally cylindrical outer boundary, at least one coil having a plurality of windings that define a loop area. A portion of the core is situated in the loop area such that the at least one coil, when energized, produces a closed magnetic flux along a flux path through the core. The length of the flux path is less than the core length.

According to another aspect of the invention, an inductive element for use in an implantable intravascular device comprises a core of magnetic material. The core has a major longitudinal dimension along a first reference axis and a core cross-section having a generally round outer boundary, with the core cross-section being defined in a first reference plane that is orthogonal to the first reference axis. The core includes a post, and at least one coil is arranged around the post, such that the coil is situated to direct a magnetic field perpendicularly to the first reference axis when energized.

A method of making an implantable intravascular device according to another aspect of the invention involves forming a generally hermetic barrier for enclosing a circuit, with the barrier having a generally cylindrical exterior surface and defines an interior form factor. An inductive element is assembled as part of the circuit to be situated within the barrier such that at least a majority of an outer surface contour of the inductive element corresponds to the interior form factor. To this end, a set of elongate windings are situated lengthwise in the barrier to direct a magnetic field along a radial direction in relation to the barrier, and a closed magnetic path is provided substantially through a permeable material for the magnetic field.

In one example embodiment, the inductive element has a cylindrical outer wall that matches the cylindrical inner wall of a compartment or other enclosure portion housing the components. In another example embodiment, the inductive element has a cylindrical outer wall that has dimensions within predefined constraints related to at least a portion of an exterior IID surface formed around the inductive element. Assembling the inductive element includes situating a set of elongate windings lengthwise in the compartment to direct a magnetic field along a radial direction in relation to the compartment; and providing a closed magnetic path substantially through a permeable material for the magnetic field. The closed magnetic path can be provided by providing a magnetic core with or without an air gap.

The approach taken by embodiments of the invention provides inductive elements that improve the volume within the form factor of an IID available for the magnetic material, while providing a relatively larger and more usable magnetic flux cross-sectional area for improved inductance and lowered AC flux density. Improving the usable volume can be accomplished by shaping much of the transformer contour to fit in a generally cylindrical space associated with the form factor. Endowing a large cross sectional area generally orthogonal to magnetic flux can be realized by winding the transformer conductors on a plane lengthwise to the IID. The direction of magnetic flux generated through the cross sectional area formed by the winding is along an axis perpendicular thereto. The relatively large magnetic flux can be useful in certain power converter topologies such as, without limitation, the flyback, SEPIC, or Cuk converters. The inductive element may also be used in other types of power circuits, such as a buck or boost regulator, or other circuits utilizing inductors or transformers.

The form factor according to certain embodiments of the invention can be defined based on the IID housing dimensions, and on the presence of other components within the enclosure portion housing the inductive element. For instance, in embodiments where additional electrical or mechanical components such as wiring, interface hardware, or circuitry is to be present in the housing in which the inductive element is situated, the form factor can take the volume constrained by these components and housing into account. In a related type of embodiment, the form factor can include space along the length of the transformer for wiring or circuitry running lengthwise past the inductive element.

Aspects of the invention enable the circuitry of an IID to achieve levels of performance in power converter circuits, among other types of circuits, that occupy the confined space of IIDs, levels which were previously unattainable using conventional power converter components in the same dimensional constraints. These advances can lead to the design of smaller and higher-performing implantable intravascular devices that are advantageously easier to implant in patients and administer more effective electrotherapy with a longer service life compared to devices based on conventional technologies.

BRIEF DESCRIPTION OF THE DRAWINGS

The invention may be more completely understood in consideration of the following detailed description of various embodiments of the invention in connection with the accompanying drawings, in which:

FIG. 1 is a perspective illustration depicting human cardiac anatomy.

FIG. 3A is a plan view of an implantable intravascular electrophysiologic therapy device according to another embodiment of the present invention.

FIG. 3B is a schematic representation of the implantable device FIG. 3A.

Figure 2A:
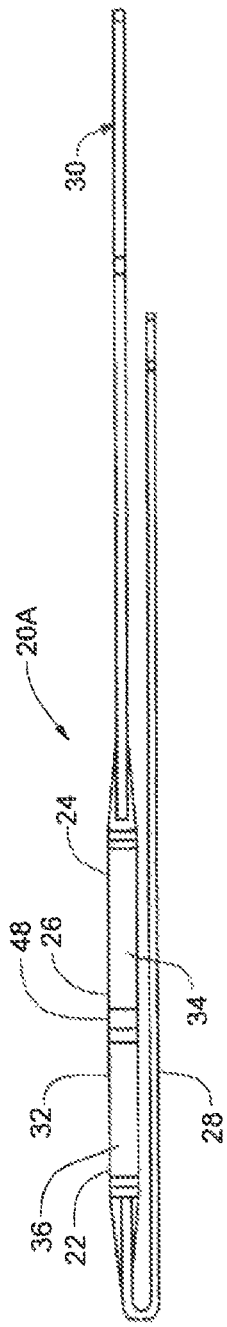
FIG. 2A is a plan view of an implantable intravascular electrophysiologic therapy device according to one embodiment of the present invention.
Figure 2B:
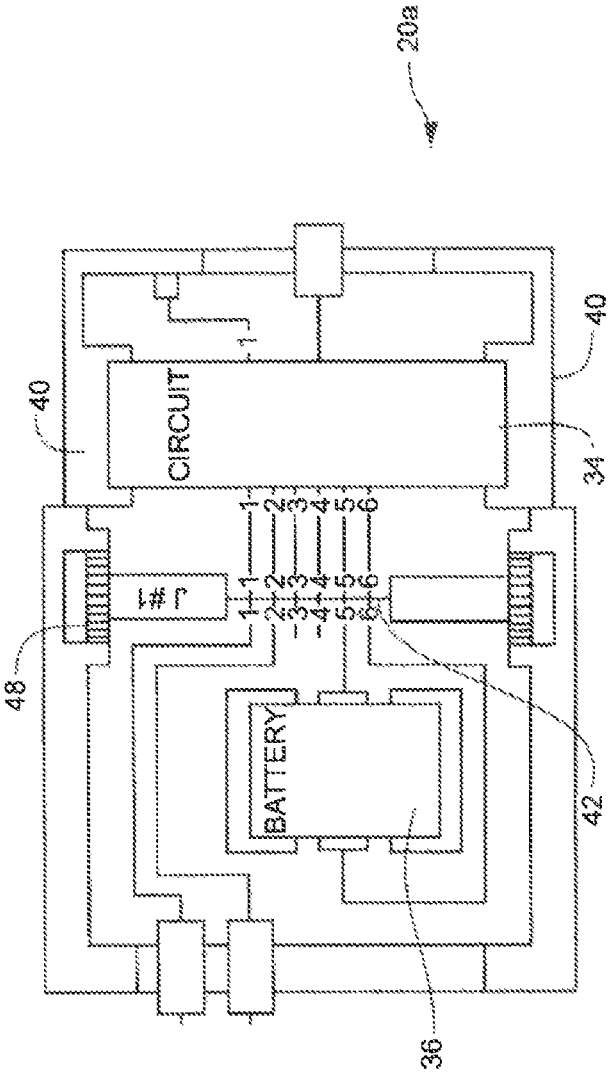
FIG. 2B is a schematic representation of the implantable device FIG. 2A.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE INVENTION

In the following detailed description of the present invention, numerous specific details are set forth in order to provide a thorough understanding of the present invention. However, it will be obvious to one skilled in the art that the present invention may be practiced without these specific details. In other instances, well-known methods, procedures, and components may not been described in detail so as to not unnecessarily obscure aspects of the present invention.

Referring now to FIG. 1, the general cardiac anatomy of a human is depicted, including the heart and major vessels. The following anatomic locations are shown and identified by the listed reference numerals: Right Subclavian 102a, Left Subclavian 102b, Superior Vena Cava (SVC) 103a, Inferior Vena Cava (IVC) 103b, Right Atrium (RA) 104a, Left Atrium (LA) 104b, Right Innominate/Brachiocephalic Vein 105a, Left Innominate/Brachiocephalic Vein 105b, Right Internal Jugular Vein 106a, Left Internal Jugular Vein 106b, Right Ventricle (RV) 107a, Left Ventricle (LV) 107b, Aortic Arch 108, Descending Aorta 109, Right Cephalic Vein 109a (not shown in FIG. 1), Left Cephalic Vein 109b, Right Axillary Vein 110a (not shown in FIG. 1) and Left Axillary Vein 110b.

One embodiment of the present invention describes intravascular electrophysiological systems that may be used for a variety of functions to treat cardiac arrhythmias with electrical stimulation. These functions include defibrillation, pacing, and/or cardioversion. In general, the elements of an intravascular implantable device for electrophysiological therapy include at least one device body and typically, but optionally, at least one lead coupled to the body. Alternatively, the intravascular implantable device may have no leads, such as for an embodiment of an intravascular implantable drug/gene therapy device, a combination intravascular implantable device that can deliver both electrical therapy and/or drug/gene therapy, or another intravascular implantable device in which a high voltage converter circuit is utilized to, for example, power drug/gene therapy delivery devices/pumps or electrically powered delivery/therapy devices.

Various examples of intravascular implantable electrophysiology devices, such as intravascular defibrillation and/or pacing devices 20 and leads 28 will be given in this description. In those examples, reference numerals such as 20a, 20b, 20c, etc., will be used to describe certain embodiments of the intravascular device 20, whereas elsewhere reference numeral 20 may be used to more generally refer to intravascular devices of the type that may be used with the present invention for providing therapy other than, or in addition to, cardiac electrophysiology. Likewise, reference number 28 may be used generally to refer to leads of a type that may be used with one embodiment of the system. Reference number 100 refers generally to vessels and/or vessel walls within the human body.

In one embodiment, device 20 includes components, known in the art to be necessary to carry out the system functions of an implantable electrophysiology device. For example, device 20 may include one or more pulse generators, including associated batteries, capacitors, microprocessors, and circuitry for generating electrophysiological pulses for defibrillation, cardioversion and/or pacing. Device 20 may also include detection circuitry for detecting arrhythmias or other abnormal activity of the heart. The specific components to be provided in device 20 will depend upon the application for the device, and specifically whether device 20 is intended to perform defibrillation, cardioversion, and/or pacing along with sensing functions, or whether the device is configured to detect and/or delivery drug/gene therapy or perform other therapeutic or diagnostic functions.

Device 20 can be proportioned to be passed into the vasculature and to be anchored within the vasculature of the patient with minimal obstruction to blood flow. Suitable sites for introduction of device 20 into the body can include, but are not limited to, the venous system using access through the right or left femoral vein or the right or left subclavian vein. In an alternate embodiment, the intravascular implantable device may be configured for use in the arterial system.

For purposes of describing the present invention, the various portions of the device 20 will be referenced to the location of those portions, the proximal portion 22, the middle portion 26 and the distal portion 24 relative to the introduction site in the femoral vein. It will be understood, however, that if an alternate access site were used to introduce the device 20, such as the subclavian veins, the various portions 22, 24 and 26 of the device 20 would be referenced relative to the inferior/superior location of the device 20 within the vascular system in the torso of a patient.

In one embodiment, the device 20 can have a streamlined maximum cross sectional diameter which can be in the range of 3-15 mm or less, with a maximum cross-sectional diameter of 3-8 mm or less in one embodiment. The cross-sectional area of device 20 in the transverse direction (i.e. transecting the longitudinal axis) can be as small as possible while still accommodating the required components. This area can be in the range of approximately 79 $mm^2$ or less, in the range of approximately 40 $mm^2$ or less, or between 12.5-40 $mm^2$, depending upon the embodiment and/or application.

In one embodiment, the cross-section of device 20 (i.e., transecting the longitudinal axis) may have a circular cross-section, although other cross-sections including crescent, flattened, or elliptical cross-sections may also be used. It can be highly desirable to provide the device with a smooth continuous contour so as to avoid voids or recesses that could encourage thrombus formation on the device. It can also be desirable to provide for a circular cross-section to aid in removal or explantation of the device that more easily permits the device to be torqued or rotated during the removal or explantation to break free of any thrombosis or clotting that may have occurred.

In one embodiment, the exterior surface of device 20 includes an electrically insulative material, layer or coating such as ePTFE. For example, it may be desirable to provide a coating that is anti-thrombogenic (e.g., perfluorocarbon coatings applied using supercritical carbon dioxide) so as to prevent thrombus formation on device 20. It may also be beneficial that the coating have anti-proliferative properties so as to minimize endothelialization or cellular in growth, since minimizing growth into or onto device 20 will help minimize vascular trauma when the device is explanted. The coating may thus also be one which elutes anti-thrombogenic compositions (e.g., heparin sulfate) and/or compositions that inhibit cellular in growth and/or immunosuppressive agents. If the housing of device 20 is conductive, this layer or coating may be selectively applied or removed to leave an exposed electrode region on the surface of the housing where necessary, such as depicted in FIGS. 2A-2B and 3A-3B.

In one embodiment, the housing of device 20, or portions thereof, have form factors designed to meet certain exterior boundary requirements. For example, an exterior boundary requirement may be a specified exterior geometry (such as a cylindrical or other suitable round shape), within certain dimensional tolerances. The housing according to this embodiment may also have an enclosure thickness specification. For example, a particular cylindrical housing may have a 10 mm outer diameter (OD) boundary specified with a tolerance, for example, of +/−5% tolerance, and a minimum wall thickness requirement of, for example, 1 mm.

Given the minimal space allowed for components, the components must themselves be dimensioned to fit within the constraints of the enclosure. With reference to the above example of the 10 mm +/−5% OD with minimum 1 mm walls, the components (including their interconnecting wiring) must fit within the form factor having a transverse dimension of 10-10(0.05)-1, or 8.5 mm. It is desirable to arrange the components within device 20 so as to make efficient use of the available space. The size and dimensions for the inductive element that can be achieved according to aspects of the invention provide additional flexibility in the selection or design of these components since the inductive element design can deliver desired performance characteristics within a space-efficient volume, leaving relatively more volume available for the components.

Examples of devices having space efficient arrangements of their contents are shown in FIGS. 2A, 2B, 3A, and 3B. One example is identified by reference numeral 20a in FIG. 2A. One embodiment of device 20a includes one or more elongate housings or enclosures 32 shown in cross-section in FIG. 2A to allow the components housed within it to be seen. In one embodiment, enclosure 32 is a rigid or semi-rigid housing optionally formed of a material that is conductive, biocompatible, capable of sterilization and capable of hermetically sealing the components contained within the enclosure 32. One example of such a material is titanium, although other materials may also be used.

Within enclosure 32 are the electronic components 34 that govern operation of the device 20a. For example, in the FIG. 2A embodiment, some components are associated with delivery of a defibrillation pulse via a lead 28, whereas other components are associated with the sensing function performed using sensing electrodes on the defibrillation lead or on a separate lead 28. Isolating high voltage components from sensing circuitry components may be desirable if electromagnetic interference (EMI) generated incidental to operation of the high voltage circuitry might interfere with performance of the sensing circuitry. Isolation may be achieved by increasing the physical separation between potentially interfering and susceptible components, by electric field shielding, by magnetic field shielding, or by a combination thereof.

Device 20a further includes an energy source, such as one or more batteries 36, for supplying power to the device. In certain embodiments of cardioverter/defibrillator devices, one or more high-voltage capacitors are provided for storing an electrical charge to be delivered to the lead(s) 28 and/or one or more exposed electrodes 40 on an exterior surface of enclosure 32. One ore more circuit interconnects 42 can provide the electrical coupling between the electronic components 34, one or more leads 28, electrode(s) 40, batteries 36 and capacitors 38.

As shown in FIG. 2A, the components of device 20a may be arranged in series with one another to give device 20a a streamlined profile. Because device 20a is intended for implantation within the patient's vasculature, some flexibility is desired so as to allow the elongate device to be easily passed through the vasculature. Flexibility may be added by segmenting device 20, such as by forming one or more breaks in enclosure 32, and by forming one or more hinge zones at each break. The hinge zones thus form dynamic flexible zones that can bend relative to the longitudinal axis of the device 20a in response to passage and/or positioning of device 20a though curved regions of the vasculature.

A second example of an arrangement of components for the intravascular implantable pacing device is identified by reference numeral 20b and shown in FIGS. 3A and 3B. Many of the components are the same as those shown in the FIG. 2A embodiment and will not be discussed again in connection with FIGS. 3A and 3B. This second embodiment differs from the first embodiment primarily in that the electronic components 34 may be included within a single area of the enclosure 32. Alternatively, the device 20b may include one or more breaks and hinge zones depending upon the components and desired anchoring location for device 20b. This configuration may be used, for example, when device 20 is intended only for performing pacing functions (and thus lacks the relatively noisy charging circuitry found in the defibrillation circuitry), or if isolation of the type shown in the FIG. 3A embodiment is not necessary to prevent noise from the charging circuit from interfering with the sensing circuits.

According to another embodiment of device 20, each segment may be separately enclosed by its own titanium (or other suitable material) enclosure in the form of containers. The components within the containers may be electrically connected by flexible circuit connects , for example. In one embodiment, the containers are connected using a flexible material such as silicone rubber filler to form hinge zones. According to another embodiment, flexible device 20 includes one or more rigid enclosures or containers 32 used to contain electronic components 34 to be implanted inside the vasculature of a patient and having the hinge zones formed of a bellows arrangement 48. Containers 32 can be of any appropriate shape, cross-section, and length, but in this example are shown to have a cylindrical shape with a diameter of approximately 3-15 mm and a length of approximately 20 mm to 75 mm. Containers 32 can be used to house electromechanical parts or assemblies to form sophisticated implantable devices such as defibrillators, pacemakers, and drug delivery systems. Any appropriate number of these containers 32 can be combined using interconnecting bellows 48. Interconnecting mechanical bellows 48 can be used, to connect a number of rigid containers 32 in order to form a flexible device 20. For many devices, this will include an arrangement of at least three containers 32.

In one embodiment, the bellows 48 can be of any appropriate shape, but can have a shape similar in cross-section to the cross-section of the container, in order to prevent the occurrence of edges or ridges that can give rise to problems such as the formation of blood clots in the vasculature. The bellows can be made of a biocompatible material similar to the containers. Any coatings used for electrically insulating the containers and/or making the containers more hemo-dynamically compatible also can be used with the bellows.

In addition to the ability of the bellows 48 to bend away from the central or long axis of device 20, the bellows 48 also allow for flexibility along the central axis of the device. The ability to flex along the central axis provides shock absorption in the long axis as well as 3-dimensional flexing. Shock absorption can help to protect device 20 and internal components during the implant process by minimizing the motion of the implanted device. Further, shock absorption can provide a 1:1 torque ratio for steering during the implant process. The shock absorption also can help during the life of device 20, as the natural movement of the body of a patient can induce some stress on the device 20.

Referring again to FIG. 2A, electronic components that are associated with the delivery of defibrillation pulses include a voltage converter circuit for converting the relatively low battery voltage to a relatively high electrotherapy voltage. One example of a relatively low battery voltage is a voltage less than about 20 volts. One example of a relatively high electrotherapy voltage is a voltage of about 50 volts or more. In one example embodiment, the battery voltage is on the order of 10 volts, and a maximum defibrillation voltage is on the order of 700-1,000 volts. Generally speaking, embodiments of the voltage converter can provide voltage boost on the order of about 5 to 300 times the voltage input to the converter. For instance, in one embodiment in which a 3 V battery is used as the energy storage for powering a boost circuit that outputs defibrillation pulses at 1,000 V, the voltage boost is a factor of 333.

A voltage converter circuit that is of a switching mode type can be used to produce the high-voltage output, which is, in turn, used to charge one or more high-voltage capacitors situated at the output of the voltage converter circuit. In some embodiments, the voltage converter circuit is capable of charging the high-voltage capacitor(s) to store at least 5 joules of energy is not more than 30 seconds. For example, in one embodiment, the voltage converter circuit can charge a high-voltage capacitor to store about 30 joules in under 10 seconds. The energy stored in the high-voltage capacitors is ultimately applied to the patient during administration of the electrotherapy.

FIGS. 4A-4D and FIGS. 5A-5G are schematic diagrams illustrating various examples of known power converter circuit topologies. These topologies are well-known by persons of ordinary skill in the relevant art, who will appreciate that while these topologies themselves can not achieve the levels of performance and efficiency as taught by the present invention, variations of these topologies made in accordance with the teachings of the present invention may be used within the spirit and scope of the invention.

Figure 4A:
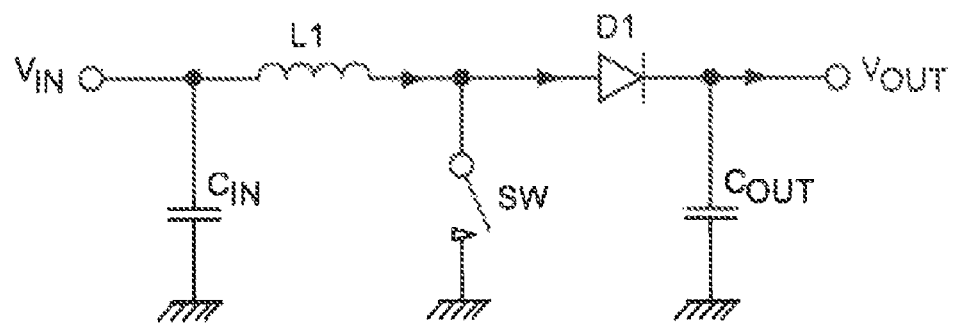
FIGS. 4A-4E are circuit diagrams illustrating various known types of switching regulators topologies.

FIG. 4A illustrates a basic boost converter topology. The boost converter of FIG. 4A utilizes a single inductor indicated at L1 to store energy in each cycle of switch SW. When switch SW closes, inductor L1 is energized and develops a self-induced magnetic field. When switch SW opens, the voltage at the L1-SW-D1 node is boosted as the magnetic field in inductor L1 collapses. The associated current passes through blocking diode D1 and charges energy storage capacitor $C_{out}$ to a voltage greater than input voltage $V_{in}$.

Figure 4B:
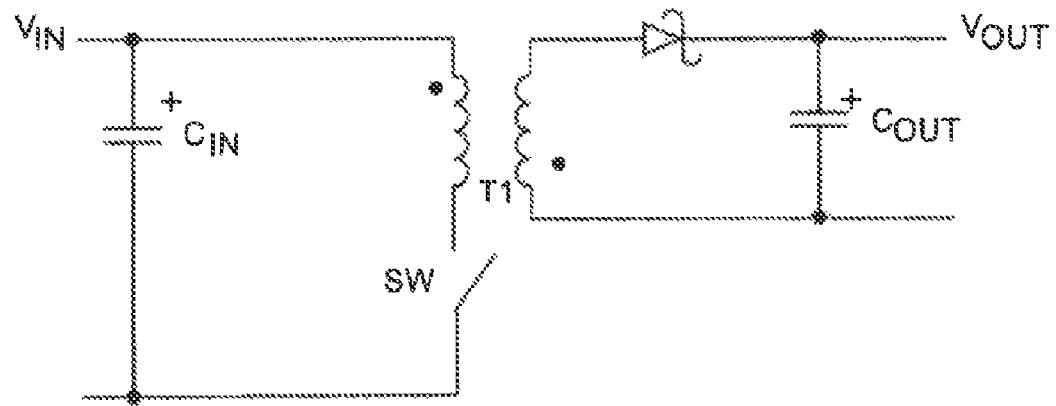

FIG. 4B illustrates a flyback converter topology. The flyback converter utilizes transformer T1 as an energy storage device as well as a step-up transformer. When switch SW is closed, the primary coil of transformer T1 is energized in similar fashion to inductor L1 of FIG. 4A. When switch SW opens, the voltage across the primary coil is reversed and boosted due to the collapsing magnetic field in the primary. The changing voltages of the primary coil are magnetically coupled to the secondary coil, which typically has a greater number of windings to further step-up the voltage on the secondary side. A typical turns ratio for IID defibrillator applications in certain embodiments is Np:Ns of about 1:15, where Np is the number of primary turns and Ns is the number of secondary turns. The high voltage across the secondary coil is rectified by the diode and stored in capacitor $C_{OUT}$.

Figure 4C:
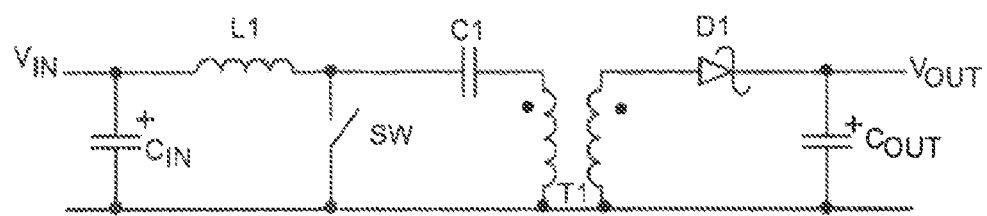

FIG. 4C illustrates a single ended primary inductance converter ("SEPIC"), which offers certain advantages over other power converter topologies. For instance, the SEPIC converter offers an advantage of not requiring significant energy storage in the transformer. Since most of the energy in a transformer is stored in its gap, this reduces the gap length requirement for the transformer. Battery voltage (from the LiSVO battery, for example) is applied at VIN and the switching element is switched at a fixed frequency and a duty cycle that is varied according to feedback of battery current into the power converter and output voltage. Voltage from the output of the step up transformer (T1) is rectified by the diode D1 to generate output voltage on COUT. The capacitance indicated at $C_{OUT}$ represents the high voltage output capacitors.

Figure 4D:
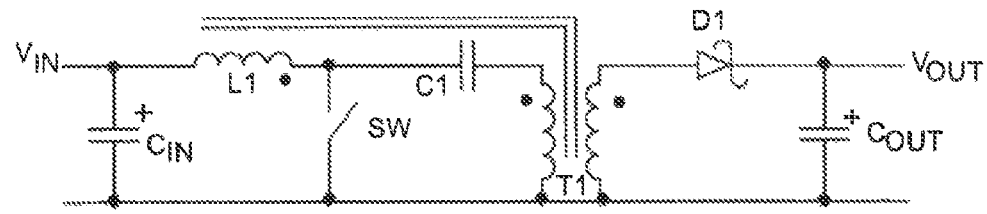

FIG. 4D illustrates a variation of the SEPIC converter of FIG. 4C. The SEPIC topology of FIG. 4D has an additional inductive component (L1). The additional inductor L1 can be implemented either discretely, or can be magnetically coupled with the high voltage transformer into a single magnetic structure, as depicted in FIG. 4D.

Figure 4E:
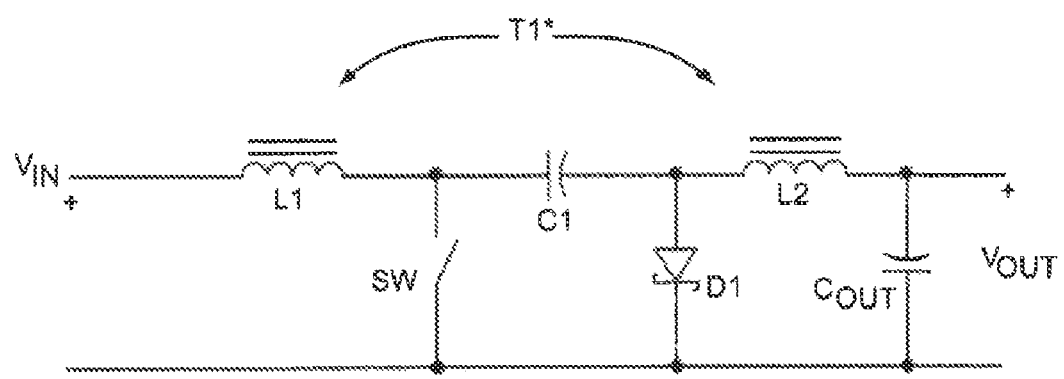

FIG. 4E illustrates a Cuk converter topology. A Cuk converter comprises two inductors, L1 and L2, two capacitors, C1 and $C_{out}$, switch SW, and diode D1. Capacitor C is used to transfer energy and is connected alternately to the input and to the output of the converter via the commutation of the transistor and the diode. The two inductors L1 and L2 are used to convert, respectively, the input voltage source (Vi) and the output voltage at capacitor $C_{out}$ into current sources. Similarly to the voltage converter circuits described above, the ratio of output voltage to input voltage is related to the duty cycling of switch SW. Optionally, inductors L1 and L2 can be magnetically coupled as indicated T1*. In this arrangement, inductors L1 and L2 may be wound on a single core.

Figure 5A:
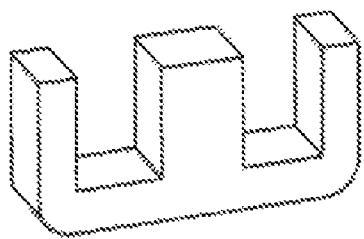
FIGS. 5A-5G are a perspective view diagrams of various inductive cores of known geometries.

FIGS. 5A-5G also illustrate various magnetic core geometries that are known in the art. Various E-shaped cores are depicted in FIGS. 5A-5D. FIG. 5A illustrates a classical E-core. The center leg's cross-section is generally larger than that of either peripheral leg, typically by a factor of two. In this geometry, the magnetic flux density is generally uniform throughout the core, provided that the coil or coils are wound around the center leg.

Figure 5B:
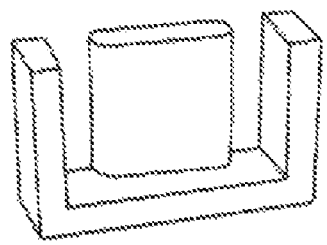
Figure 5C:
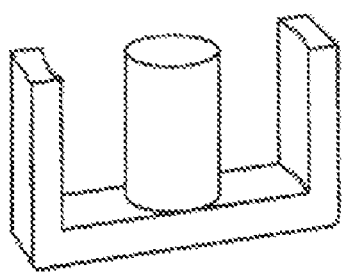

FIG. 5B illustrates an EFD core, in which the center leg is narrower in one dimension but wider in an orthogonal dimension. This type of geometry facilitates lower-profile inductive elements. FIG. 5C illustrates an ER core, in which the center leg has a round cross-section.

Figure 5D:
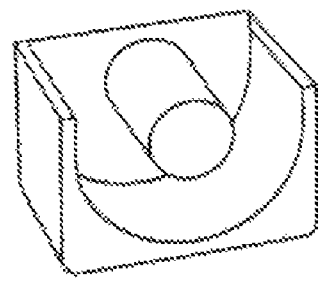
Figure 5E:
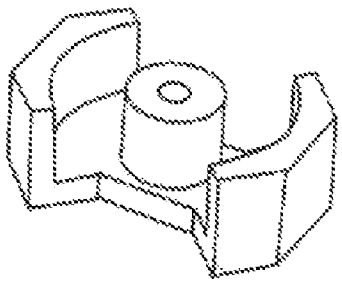

FIG. 5D illustrates an EP core, in which a generally cylindrical center leg is partially surrounded by core material for the magnetic flux return path. Between the center leg and surrounding portion is space in which the coil or coils would be situated. FIG. 5E illustrates a pot core which, like the EP core, has a center leg at least partially surrounded by core material with space therebetween for situating the coil(s).

Figure 5F:
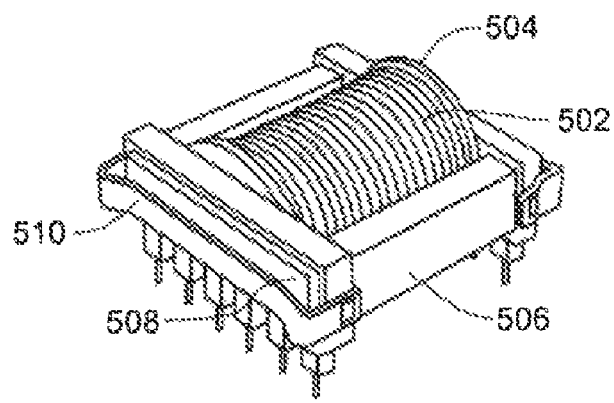

FIG. 5F is a diagram illustrating an inductor or transformer assembly using a two-piece core construction. Coil(s) 502 is wound around bobbin 504, which is placed such that coil(s) 502 is positioned around the center leg of E core 506. An I-shaped core 508 is secured to the open end of E core 506 using clip 510. E core 506 and I core 508 positioned in this way produce a structure in the form of "EI" in which there is magnetic material to guide a closed flux path through the center leg of E core 506 and through the center of coil(s) 502, and returning through the peripheral legs of E core 506.

Figure 5G:
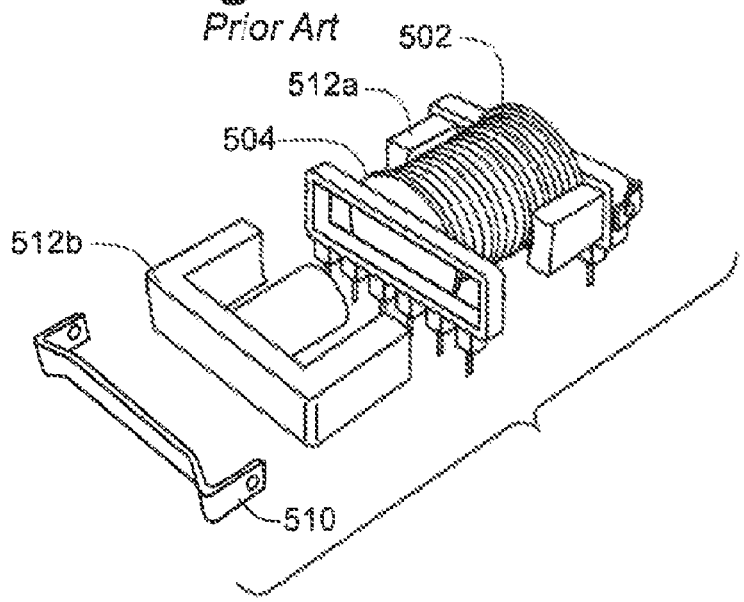

FIG. 5G illustrates another inductive element assembly utilizing a two-part core. In FIG. 5G, a pair of opposing ER cores 512a and 512b is used. Coil(s) 502 are wound around bobbin 504, which has a length that is longer than the center leg of either ER core. When assembled, the pair of ER cores come together to complete the magnetic flux path. When an air gap is needed, the center leg of one or both E-type cores can be shorter than either of the peripheral legs. Similar structures can be assembled using pot cores, different types of E cores, and other variants thereof. As described above, these conventional geometries are not well-suited for use in IIDs.

Figure 6:
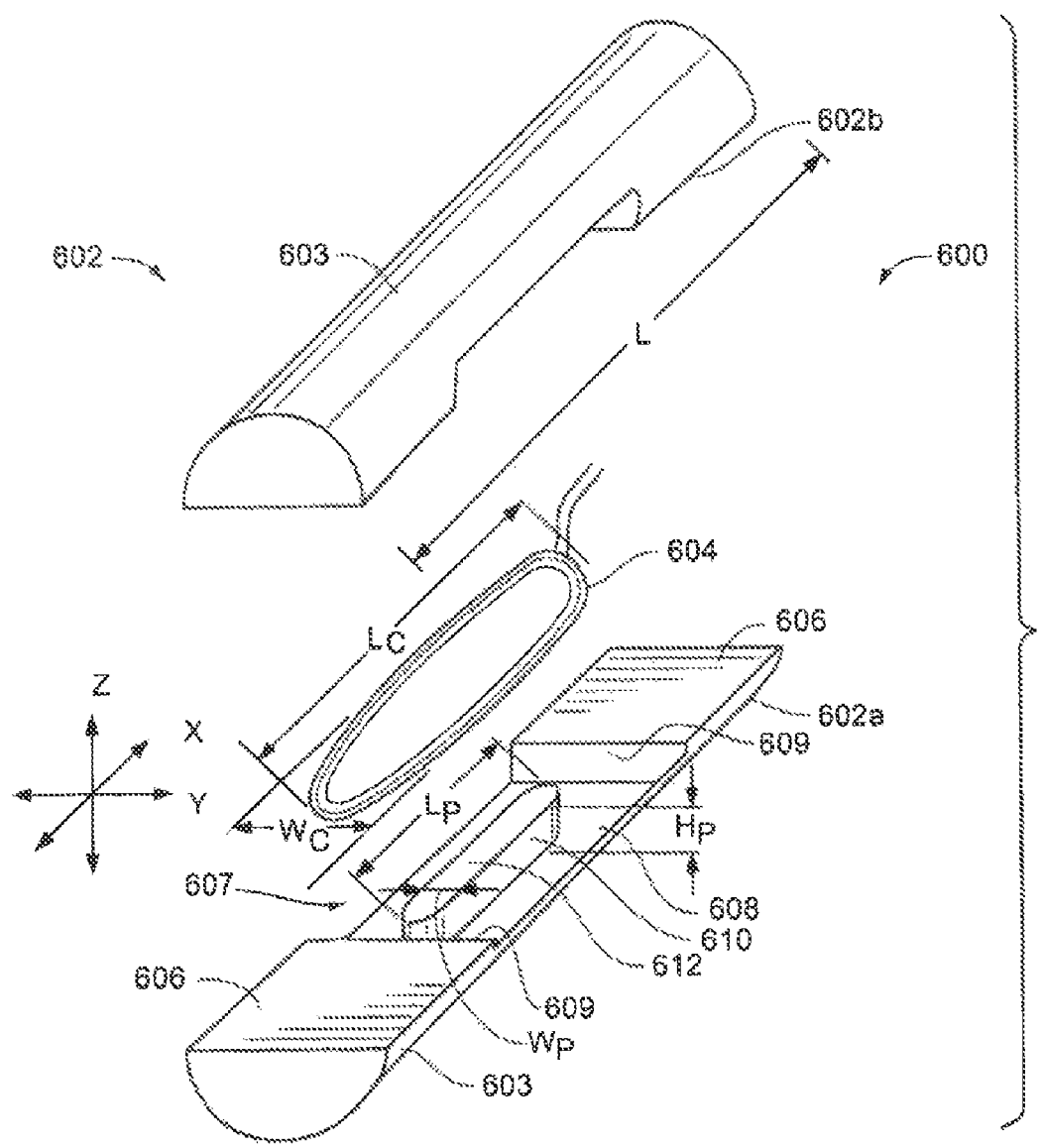
FIG. 6 is an exploded view diagram illustrating a narrow form factor inductive element assembly according to one aspect of the invention.

FIG. 6 is a diagram illustrating inductive element 600 according to one embodiment of the invention. Inductive element 600 has a narrow form that is well-suited for use inside the housing of an intra-vascular implantable device such as device 20. In one exemplary embodiment, the outer surface of inductive element 600 generally conforms to an inner surface of a portion of enclosure 32. In this arrangement, a large amount of interior volume of the portion of enclosure 32 that houses inductive element 600 is used for guiding magnetic flux. This provides a relatively larger inductance for inductive element 600, as compared with an inductive element of conventional geometry that would not occupy as large a proportion of interior volume space within a comparable portion of enclosure 23 as inductive element 600.

Inductive element 600 is assembled from a generally cylindrical magnetic core 602 having an outer surface 603, and a major length/situated along longitudinal reference axis x, and a generally round (e.g., circular, elliptical, etc.) cross-section situated along the transverse y-z plane. Magnetic core 602 is itself composed of two halves, lower half 602a; and upper half 602b. Situated within core halves 602a and 602b are one or more coils of wire 604. Although only a single coil is depicted for the benefit of clarity, it is to be understood that a plurality of coils may be used to provide mutually-coupled transformer windings.

Each core half 602a and 602b has a mating surface 606 and a cut-away portion 607. Cut-away portion 607 is defined by bottom surface 608, opposing walls 609, and post 610. Post 610 protrudes from bottom surface 608 along reference axis z, and has a major length lp along longitudinal reference axis x, minor width wp along reference axis y, and protruding height hp along reference axis z. Post 610 also has a top surface 612 that may be generally co-planar with mating surface 606.

In a related embodiment, top surface 612 is not co-planar with mating surface 606; instead, top surface 612 is recessed relative to mating surface 606. In this configuration, top surface 612 of core half 602a does not intimately contact the corresponding top surface of core half 602b when the core halves are joined. The resulting structure has an air gap between the opposing top surfaces 612. The height of post 610 of either or both core halves 602a or 602b may be designed to provide an air gap of a particular size to achieve desired magnetic properties for inductive element 600. As described above, the gap length determines the amount of energy that may be stored by inductive element 600, and also affects the inductance of inductive element 600.

In another embodiment, core halves 602a and 602b are not identical. For example, bottom core half 602a may have a post, while upper core half 602b has no post. In this example embodiment, the post can have a post height that is taller than the height of opposing walls 609 in the z axis. In one related embodiment, the post height is about double the height of opposing walls 609 in the z axis.

Coil 604 has a major length lc along reference axis x and a minor width we along reference axis y. Thus, coil 604 has elongate, or oblong, windings that define a correspondingly elongate, or oblong, loop area situated longitudinally along the major axis of core 602. In one embodiment, coil 604 is dimensioned such that, when inductive element 600 is assembled, no winding of coil 604 protrudes beyond the outer cylindrical periphery of core 602. As depicted in FIG. 6, coil 604 is situated to around, or in circumscribing fashion, to protrusion 610 in the x-y reference plane. In one example embodiment, coil 604 is pre-formed with sufficient tolerance to permit sliding coil 604 over post 610. In another embodiment, coil 604 is actually wound around post 610.

In operation in this embodiment, the major magnetic flux component produced by current in coil 604 travels in a first direction along the z reference axis through protrusion 610. Minor magnetic flux components (summing to nearly equal the major magnetic flux component) return to complete the magnetic circuit through the remainder of core 602 (i.e. generally perpendicularly through mating surfaces 606 in the opposite direction along the z reference axis. As can be seen from the geometry of inductive element 600, coil 604 produces the major flux component along an axis that is generally perpendicular to length l of the major axis of core 602 (i.e., in the y-z plane).

Generally speaking, the inductance of a coil of wire is a function of the relative permeability, the number of windings in the coil, the loop area defined by the coil, and the height dimension of the coil structure. The inductance is directly proportional to the loop area, and inversely proportional to the height dimension of the coil structure. Therefore, in qualitative terms, a coil having a greater loop area and a shorter coil structure height will produce an element having a relatively greater inductance per unit length of wire comprising the coil. Accordingly, in the constrained elongate form factor of an implantable intravascular device, the geometry of coil 604 provides desirable inductive characteristics. The elongate or oblong shape of the windings of coil 604 provide a relatively large loop area and a relatively small coil structure height. For example, in one embodiment, the major oblong loop dimension $l_c$ of coil 604 is greater than the height of coil 604 by a factor of 2.3. In a related embodiment, the square root of the loop area of coil 604 is greater than the height of coil 604 by a factor of 1.7.

In one embodiment, the loop area of coil 604 is greater than the cross-sectional area of inductive element 600 (the cross-section being taken in a plane perpendicular to the major length dimension l of inductive element 600, such as in the y-z plane). In a related embodiment, the loop area of coil 604 is greater than the cross-sectional area of the form factor in which inductive element 600 is enclosed.

By comparison, an inductive element having a solenoid-shaped coil (in which the coil structure length is similar to, or greater than, the loop area) such as the geometry of a coil structure used in a pot-type core or in a core that is assembled with a wound bobbin, would require significantly more wire length to achieve the same inductance as that of similarly-dimensioned coil 604. This increased amount of wire corresponds to a greater electrical resistance of the inductive element and, consequently, reduced operating efficiency as an energy storage element.

The geometry of core 602 provides further advantages relative to conventional pot cores when dimensioned to fit in the form factor of IIDs. For example, core 602 provides a shorter flux path and a greater cross-sectional area for the magnetic flux than does the conventional pot core. In one example embodiment, the total length of the closed magnetic flux path is less than the length l of core 602. This type of magnetic circuit geometry of core 602 advantageously has less magnetic reluctance, and thus more inductance per unit of core volume as compared against the pot core geometry.

Comparing the core geometry of core 602 against conventional E- or C-type cores, core 602 is optimized to operate in the IID form factor. Thus, core 602 has more magnetic material for a greater cross-sectional area for the magnetic flux than does a similarly-dimensioned E- or C-type core. In one example embodiment, the sum of the areas of surfaces 606 and 612 is greater than the area defined by the outer boundary of the cross-section of inductive element 600 (the cross-section being taken in a plane perpendicular to the major length dimension l of inductive element 600, such as in the y-z plane). In a related embodiment, the sum of the areas of surfaces 606 and 612 is greater than the cross-sectional area of the form factor enclosing inductive element 600. In another embodiment, the cross-sectional area of post 610, such as the area of surface 612 alone, for example, is greater than the area defined by the outer boundary of the cross-section of inductive element 600.

In another related embodiment, the sum of the loop area of coil 604 and the cross-sectional area of the portion of core 602 that is co-planar with coil 604 and carries the returning magnetic flux, exceeds the area defined by the outer boundary of the cross-section of inductive element 600. In a related embodiment, the total area of the cross-section of the magnetic flux forward and return paths through core 602 is greater than the outer boundary of the cross-section of inductive element 600.

Figure 7A:
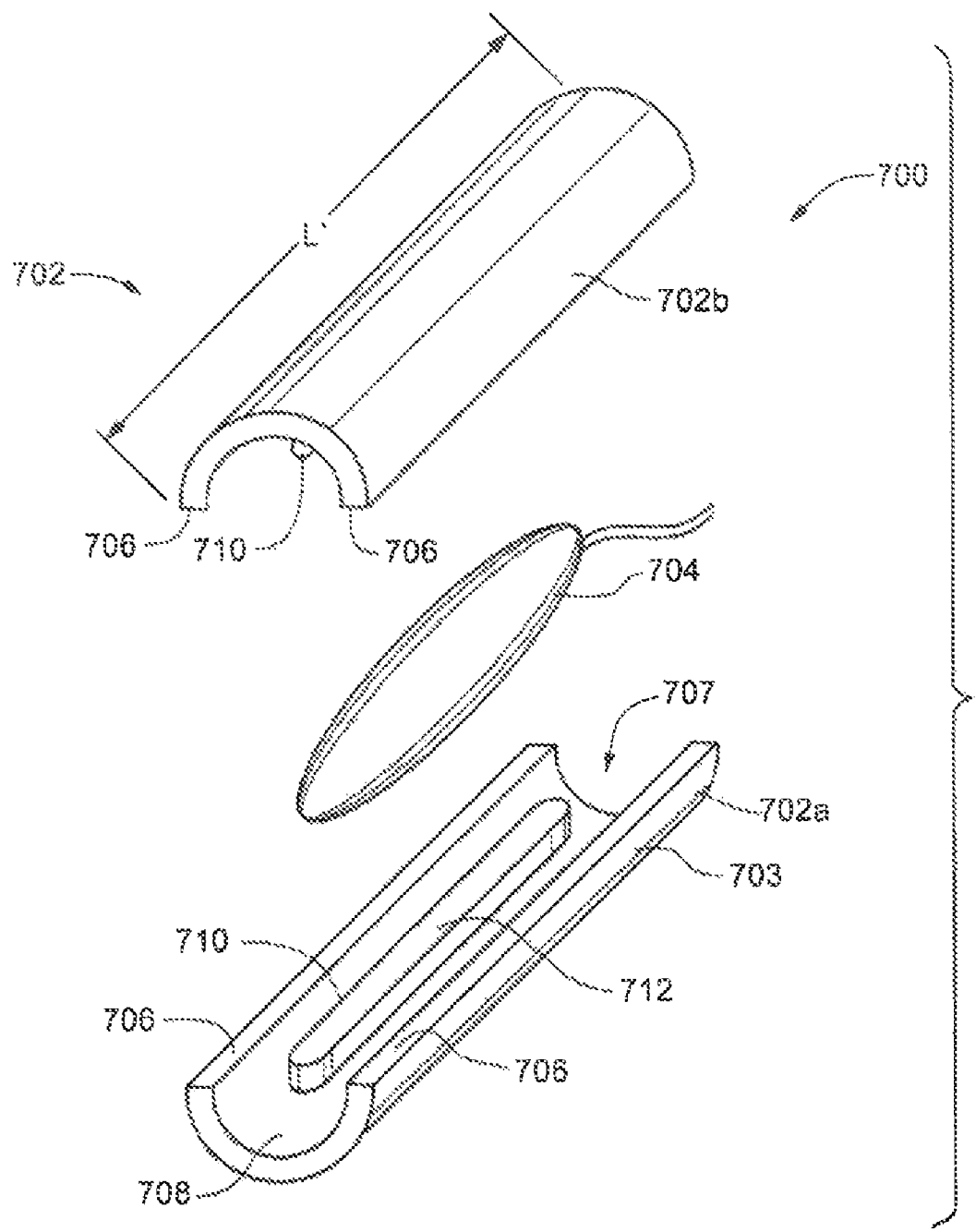
FIG. 7A is an exploded view diagram illustrating another narrow form factor inductive element assembly according to another aspect of the invention.

FIG. 7A is a diagram of inductive element 700 according to another embodiment. Inductive element 700 includes a generally cylindrical core 702 having lower half 702a and upper half 702b, and coil 704. Coil 704 is substantially similar to coil 604 of FIG. 6 in that both coils have a generally elongate shape with a major dimension of the coil situated along the major dimension of the corresponding cylindrical core.

A portion of each core half 702a and 702b has a cross-sectional shape that generally resembles the Cyrillic character "Э" (Unicode character 0x042D). Each core half 702a and 702b has a mating surface 706 that extends along the major length l' of inductive element 700, and cavity 707 defined by generally cylindrical interior surface 708, and post 710 that protrudes from interior surface 708. When core halves 702a and 702b are interfaced with one another to produce a core assembly, the interfaced core halves define a pair of opposing cavities having a D-shaped cross-section and a length along the major dimension of core 702.

The structure and geometry of the core 702 of inductive element 700 can be further described as a cylindrical shell having length l', and inner and outer diameters defined by outer cylindrical surface 703 and inner cylindrical surface 708. Post 710 substantially bridges the diameter over a portion of the length. Post 710 may fully bridge the diameter in an embodiment without an air gap in the post. Otherwise, where an air gap is desired, post 710 mostly bridge the diameter, save for the air gap.

Coil 704 (and optionally, additional coils) are assembled to fit in cavity 707 and to be situated around, i.e., in circumscribing fashion, post 710. In one embodiment coil 704 does not protrude beyond the ends of core 702 (i.e., beyond the l' dimension). Post 710 has a top surface 712 that, like top surface 612, may be co-planar, or recessed, relative to mating surface 706. Thus, assembled inductive element 700 may or may not have an air gap. In one embodiment, mating surface 706 has a surface area that is equal to the surface area of top surface 712, such that the return path for the magnetic flux through the core has the same reluctance as the forward path. In a related embodiment, the sum of the surface areas of surfaces 706 and 712 is greater than the area defined by the outer boundary of the cross-section of inductive element 700 (the cross-section taken perpendicularly to length l'). In another related embodiment, mating surface 706, alone, has a surface area greater than the area defined by the outer boundary of the cross-section of inductive element 700.

Figure 7B:
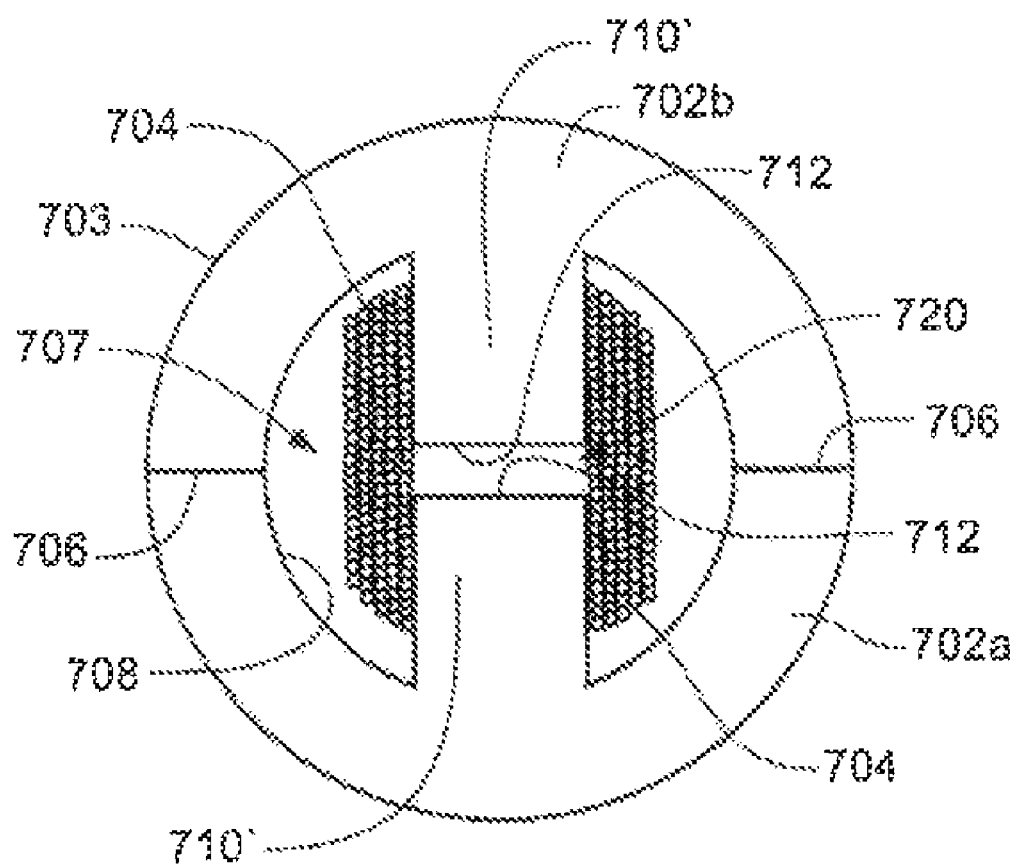
FIG. 7B is a cross-sectional view of the assembled inductive element of FIG. 7A.

FIG. 7B is a cross-sectional view illustrating assembled inductive element 700. Core halves 702a and 702b are positioned together such that mating surfaces 706 are in intimate contact. Top surfaces 712 of posts 710', as depicted, are recessed relative to mating surfaces 706, producing air gap 720. Coil 704 is situated around, or in circumscribing fashion, about posts 710' within cavity 707.

Operation of inductive element 700 is similar to that of inductive element 600. Current in coil 704 produces magnetic flux in core 702. A major component of the flux passes through protrusion 710. The return flux path is distributed through the remainder of core 702. The enclosed geometry of core 702 along the cylindrical wall provides additional magnetic shielding compared to that of core 602. In a related embodiment, the ends of core 702 are also closed to thereby virtually eliminate any field fringing effects occurring beyond the boundary of the core. This embodiment is, in a sense, a combination of core 602 (having closed ends) and core 702 (having a closed cylindrical wall).

Figure 8:
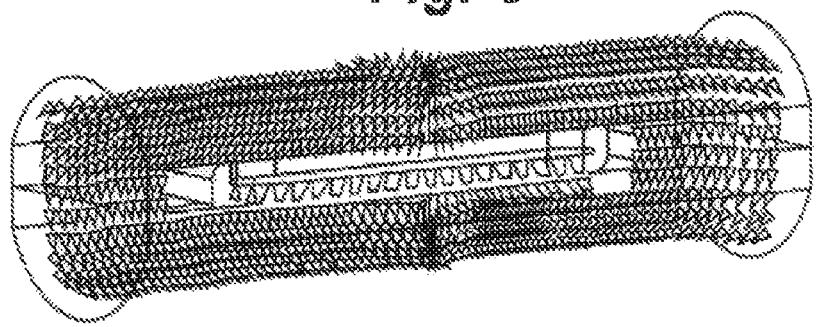
FIG. 8 is a diagram illustrating simulated magnetic flux density throughout the core of an exemplary inductive element according to one embodiment of the invention, such as the inductive element of FIG. 6.
Figure 9:
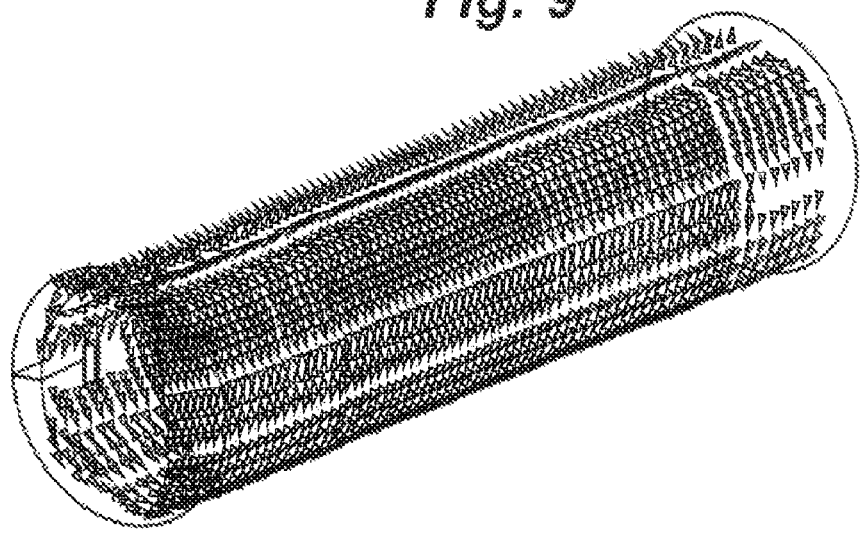
FIG. 9 is a diagram illustrating simulated magnetic flux density throughout the core of an exemplary inductive element according to another embodiment of the invention, such as the inductive element of FIGS. 7A-7B.

FIGS. 8 and 9 illustrate the magnetic flux density throughout each of cores 602 and 702, respectively, based on computer-aided simulation results. A comparison of the model of FIG. 9 against that of FIG. 8 suggests core 702 provides a more uniform magnetic flux density throughout its volume than core 602. This may be explained qualitatively from the fact that core 702 provides a greater surface area for the magnetic flux return path, and a shorter overall magnetic flux path. Additionally, in core 702, points along the return path are generally more equidistant from the forward magnetic flux path compared with those of core 602. Thus, core 702 provides a magnetic circuit geometry with less reluctance and greater magnetic flux density uniformity than core 602.

For any of the voltage converter circuits described herein, as well as for other power circuits utilizing an inductive element according to the invention, the inductive element can maximize converter circuit performance and efficiency in view of the substantial geometric constraints. More generally, in power converters that utilize mutually coupled coils, such as the certain Cuk, SEPIC or flyback topologies, for example, the multiple coils can be accommodated by embodiments of the inductive element of the invention. Persons skilled in the relevant arts will appreciate that the inductive elements of the invention can be constructed using known techniques and materials, such as, for example, from powdered ferrite stock. A variety of magnetic permeability ranges for the core material may be used for different applications.

Embodiments of the invention enable certain operational performance metrics to be achieved in the confined geometry of IIDs that otherwise would not be attainable using conventional inductive elements in the power converter circuitry. For instance, an IID defibrillator according to one embodiment, which has a diameter of less than 15 mm, and in one embodiment less than about 8 mm, utilizes a Cuk or SEPIC power converter circuit having an inductive element of a type described above. This power converter circuit can convert a battery voltage into an electrotherapy voltage that is least ten times greater than the battery voltage, and output energy at that voltage at a rate of at least 1 W with an operating efficiency of at least 60% when the battery power source is fully charged.

Figure 10:
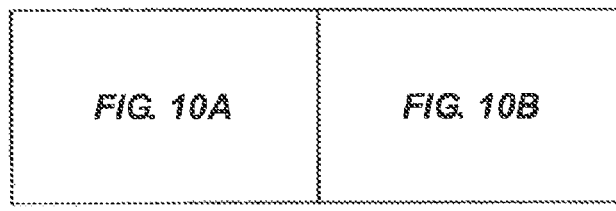
FIGS. 10 and 10A and 10B is a diagram illustrating a power converter circuit and a portion of a control system for the power converter according to one example embodiment.
Figure 10A:
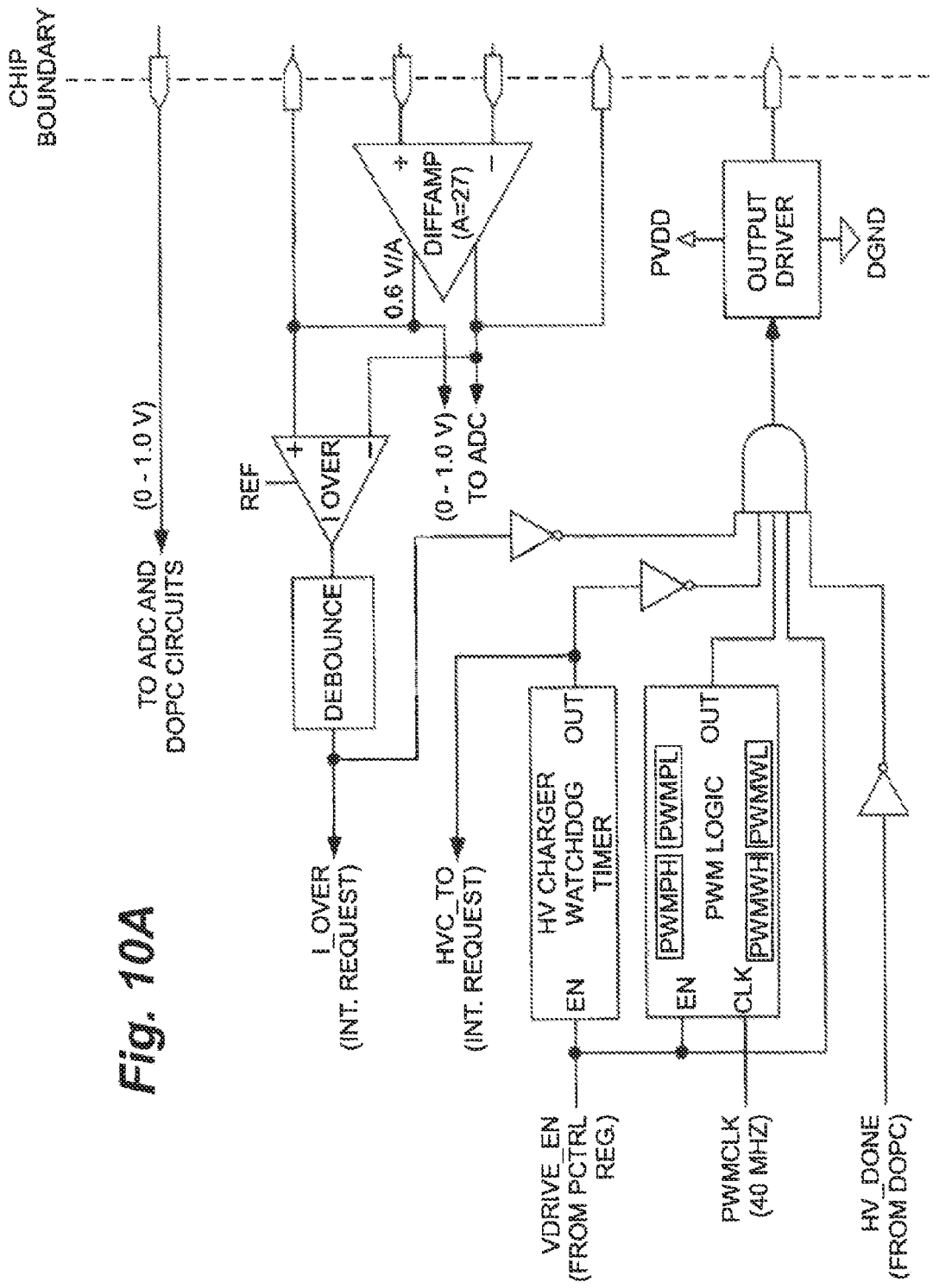
Figure 10B:
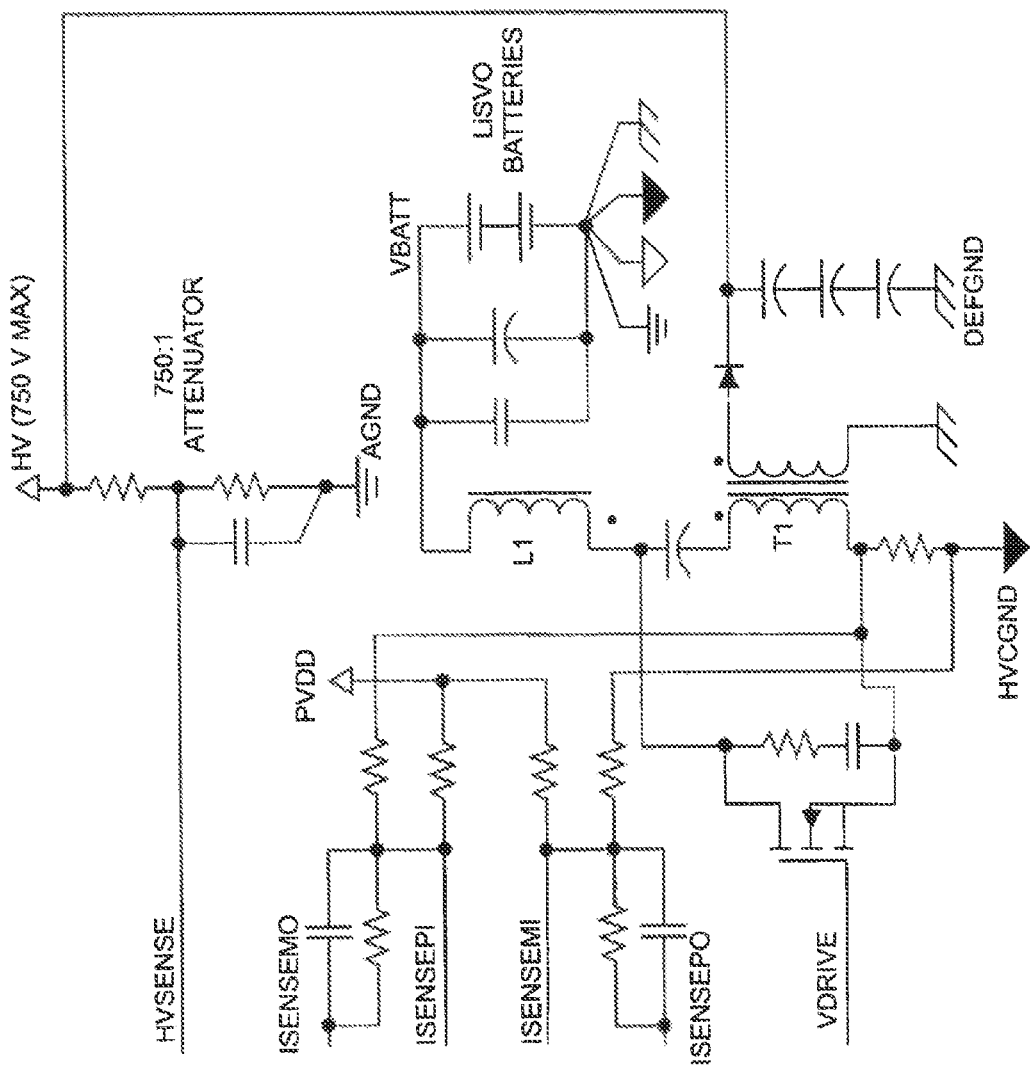

FIGS. 10 and 10A-10B is a diagram illustrating a power converter circuit and a portion of a control system for the power converter according to one example embodiment. The power converter topology in this example is a SEPIC power converter circuit in which inductor L1 is mutually coupled to transformer T1. Inductor L1 and transformer T1 are formed as a multi-winding inductive element having a geometry according to the embodiments described above. In this example, all of the windings are situated around a common core.

Transistor Q1 operates in a switching mode that periodically energizes inductor L1 and the primary winding of transformer T1. The current through the primary winding of transformer T1 is sensed and fed to the control circuit as illustrated. Also, the output voltage HV is sensed and fed to the control circuitry. The output voltage is controlled by varying the duty cycling of the drive signal to switching transistor Q1.

By sensing both, the output voltage, and the current through the primary winding of transformer T1, the power converter of this example can be dynamically controlled to adjust its operating conditions so as to provide the desired output at the best possible efficiency under the circumstances. The circumstances may vary due to internal or external events. For instance, the battery voltage tends to drop as the battery's energy is consumed over its life. In one embodiment, the control circuit adjusts operation of the power converter to accommodate this event.

In the embodiment illustrated in FIGS. 10 and 10A-10B, the functional blocks depicted on the left-hand side of the Chip Boundary are implemented in an application-specific integrated circuit (ASIC). The circuit portion on the right-hand side of the Chip Boundary is implemented using discrete electronic components. In a related embodiment, groups of resistors, such as the six resistors used to condition the current sense signal, are implemented using a resistor network such as a thin-film resistor network on a common substrate. This type of arrangement advantageously provides well-matched resistors having similar temperature coefficients and similar heating during operation.

The present invention may be embodied in other specific forms without departing from the spirit of the essential attributes thereof. For example, aspects of the invention are not limited to use exclusively in implantable defibrillator devices. Other types of devices having a small form factor and utilizing an inductive element may also benefit from these aspects of the invention. For example, implantable drug delivery devices, electrostimulation devices, patient monitoring and data communication devices, and the like, may utilize one or more inductive elements according to the invention.

Additionally, the invention is not necessarily limited to power converter circuits. Inductive elements according to aspects of the invention may be utilized in other types of circuits and for a variety of other functions such as, for example, for filtering, matching signal impedance, and the like. Therefore, the illustrated embodiments should be considered in all respects as illustrative and not restrictive, reference being made to the appended claims rather than to the foregoing description to indicate the scope of the invention. For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. An implantable intravascular medical device comprising:
   a structure that defines a form factor having an elongate geometry including a form factor length and a cross-section defined perpendicularly to the form factor length; and
   a circuit situated within the form factor and including an inductive element;
   wherein the inductive element includes:
      a core of magnetic material having a core length and a core cross-section defined perpendicularly to the length; and
      a coil having a plurality of windings that define a loop area;
      wherein a portion of the core is situated in the loop area such that the coil, when energized, produces a magnetic flux in the core along a forward path and a return path; and
      wherein a sum of a total cross-sectional area of the magnetic flux in the forward path and a total cross-sectional area of the magnetic flux in the return path is greater than an area of the core cross-section.

2. The implantable intravascular medical device of claim 1, wherein the sum of a total cross-sectional area of the magnetic flux in the forward path and the total cross-sectional area of the magnetic flux in the return path is greater than an area of the cross-section of the form factor.

3. The implantable intravascular medical device of claim 1, wherein the loop area is greater than at least one area selected from the group consisting of: an area of the core cross-section, and an area of the cross-section of the form factor.

4. The implantable intravascular medical device of claim 1, wherein:
   the implantable intravascular device includes a defibrillator and the circuit is a power converter circuit;
   the form factor is generally cylindrical and has a generally circular cross-section, and the structure that defines the form factor includes a housing having a generally cylindrical outer surface and an inner surface that defines at least a portion of the form factor, wherein the housing includes a generally hermetic barrier;
   the inductive element is a transformer having a plurality of mutually-coupled coils that are entirely arranged within a boundary defined by the outer surface of the inductive element;
   the core has a generally cylindrical outer boundary and a post having an oblong cross-sectional boundary with a major oblong dimension situated lengthwise along the generally cylindrical outer boundary, the post having a post height situated radially in relation to the generally cylindrical outer boundary, and the coils being situated around the post; and
   the core comprises a pair of core halves, wherein when the core is assembled from the pair of core halves, the core halves interface at respective mating surfaces, and the post comprises a pair of post portions, each post portion corresponding to one of the core halves and arranged such that the post includes an air gap.

5. An inductive element, comprising:
   a core of magnetic material having a core length and a generally cylindrical outer boundary; and
   at least one coil having a plurality of windings that define a loop area;
   wherein a portion of the core is situated in the loop area such that the at least one coil, when energized, produces a closed magnetic flux along a flux path through the core, wherein a length of the flux path is less than the core length.

6. The inductive element of claim 5, wherein:
   the inductive element is a transformer having a plurality of mutually-coupled coils that are entirely arranged within the outer boundary;
   the core includes a post having an oblong cross-sectional boundary with a major oblong dimension situated lengthwise along the generally cylindrical outer boundary, the post having a post height situated radially in relation to the generally cylindrical outer boundary, and the coils being situated around the post; and
   the core comprises a pair of core halves, wherein when the core is assembled from the pair of core halves, the core halves interface at respective mating surfaces, and the post comprises a pair of post portions, each post portion corresponding to one of the core halves and arranged such that the post includes an air gap.

* * * * *